(12) United States Patent
Kuo (10) Patent No.: US 8,024,198 B2
(45) Date of Patent: Sep. 20, 2011

(54) SYSTEM AND METHOD FOR PROVIDING OPTIMIZED PATIENT REFERRALS

(75) Inventor: Eric Kuo, Foster City, CA (US)

(73) Assignee: Align Technology, Inc., San Jose, CA (US)

( * ) Notice: Subject to any disclaimer, the term of this patent is extended or adjusted under 35 U.S.C. 154(b) by 377 days.

(21) Appl. No.: 12/258,125

(22) Filed: Oct. 24, 2008

(65) Prior Publication Data

US 2010/0106518 A1 Apr. 29, 2010

(51) Int. Cl.
G06Q 10/00 (2006.01)
G06Q 50/00 (2006.01)
(52) U.S. Cl. .......................................................... 705/2
(58) Field of Classification Search .................. 705/2, 3
See application file for complete search history.

(56) References Cited

U.S. PATENT DOCUMENTS

| 2002/0059587 | A1* | 5/2002 | Cofano et al. ................. 725/35 |
| 2004/0019579 | A1* | 1/2004 | Herz et al. ........................ 707/1 |
| 2005/0148830 | A1* | 7/2005 | Arnett ........................... 600/300 |
| 2005/0271996 | A1* | 12/2005 | Sporbert et al. ................ 433/24 |
| 2008/0077461 | A1* | 3/2008 | Glick ................................ 705/7 |
| 2009/0276242 | A1* | 11/2009 | Waisbren .......................... 705/2 |

* cited by examiner

*Primary Examiner* — Gerald J. O'Connor
*Assistant Examiner* — Trang Nguyen (57) ABSTRACT

In particular embodiments, method, apparatus and system for generating a doctor profile based on one or more parameters associated with the doctor treatment information, generating a patient dental profile based at least in part on a weighting of a plurality of orthodontic-related treatment parameters, and providing one or more doctor referrals based on the generated doctor profile and the generated orthodontic patient profile are provided.

32 Claims, 8 Drawing Sheets

| Digit>> Value | 1st Cuspid Relationship (Right) | 2nd Cuspid Relationship (Left) | 3rd Overbite | 4th Crowding / Spacing (Upper) | 5th Crowding / Spacing (Lower) |
|---|---|---|---|---|---|
| 1 | Severe Class II 101 | Severe Class II | Severe Open Bite | Severe Spacing | Severe Spacing |
| 2 | Moderate Class II 102 | Moderate Class II | Moderate Open Bite | Moderate Spacing | Moderate Spacing |
| 3 | Mild Class II 103 | Mild Class II | Mild Open Bite | Mild Spacing | Mild Spacing |
| 4 | Class I 104 | Class I | Normal Overbite | No Discrepancy | No Discrepancy |
| 5 | Mild Class III 105 | Mild Class III | Mild Deep Bite | Mild Crowding | Mild Crowding |
| 6 | Moderate Class III 106 | Moderate Class III | Moderate Deep Bite | Moderate Crowding | Moderate Crowding |
| 7 | Severe Class III 107 | Severe Class III | Severe Deep Bite | Severe Crowding | Severe Crowding |

| Digit>> | 1st Cuspid Relationship (Right) | 2nd Cuspid Relationship (Left) | 3rd Overbite | 4th Crowding / Spacing (Upper) | 5th Crowding / Spacing (Lower) |
|---|---|---|---|---|---|
| Value | | | | | |
| 1 | | | | | |
| 2 | | | Moderate Open Bite 2 | Moderate Spacing 2 | |
| 3 | | | | | |
| 4 | | | | | |
| 5 | Mild Class III 5 | | | | Mild Crowding 5 |
| 6 | | Moderate Class III 6 | | | |
| 7 | | | | | |

SYSTEM AND METHOD FOR PROVIDING OPTIMIZED PATIENT REFERRALS

BACKGROUND

The present disclosure is related generally to the field of orthodontics. More specifically, the present disclosure is related to methods and system for providing optimized patient referrals for orthodontic treatments.

A primary objective of orthodontics is to realign patients' teeth to positions where the teeth function optimally and have an aesthetic appearance. The goal of a doctor is to take the patient from their current condition ("initial" or "starting dentition") to a final condition ("treatment goal"). The result achieved is known as the "treatment outcome." There may be many ways to achieve the goal and these are known as "treatment options." The methodologies used by the doctor to get the patient to the goal are known as the "treatment plan."

Often times, doctors establish the goal as "ideal" and discontinue treatment when they are as close as they can possibly get to the ideal. However, more recently with the growing use of 3-D computer graphics software services and programs in dentistry, the doctor can actually establish a custom treatment goal specific to each individual patient, and this goal may be a limited treatment goal and not ideal in every component of the bite. This is important because if the doctor is able to achieve 100% of the intended limited goal, the treatment may still be deemed a success, whereas it may be possible that if the doctor only achieves 75% of a completely "ideal" treatment goal, the treatment might not be deemed a success even though the amount of measured improvement on an absolute scale in the latter situation might be higher than in the limited treatment situation.

Furthermore, it may be desirable to have available methods and systems for patients, doctors, and/or dental professionals to determine optimal orthodontic professional referrals. The dental professionals may be chosen based on numerous criteria including, but not limited to, initial patient dental parameters, patient treatment preference, treatment difficulty, treatment success rate, historical information related to the type of treatment performed, geographical location of the orthodontic professional, and the like.

In view of the foregoing, it would be desirable to have methods and systems to provide optimized referrals of patients to dental professionals, either for prospective patients to self-refer themselves to dental professionals, or for dental professionals to refer prospective patients to other dental professionals.

SUMMARY

In one aspect, method, apparatus or system for generating a doctor profile based on one or more parameters associated with the doctor's treatment information, generating an patient dental profile based at least in part on a weighting of a plurality of orthodontic-related treatment parameters, and providing one or more doctor referrals based on the generated doctor profile and the generated orthodontic patient profile is provided.

In a further aspect, method, apparatus or system for generating an orthodontic patient profile, performing a treatment assessment based on the patient profile to determine a treatment profile, querying a database based on the treatment profile, and generating a list of referral doctors associated with the treatment profile is provided.

In yet another aspect, method, apparatus or system for determining one or more treatment parameters associated with an orthodontic condition of a patient, querying a database for each of the one or more treatment parameters, generating a query result for each treatment parameter, and weighting each of the query result based on a predetermined weighting parameter is provided.

These and other features and advantages of the present disclosure will be understood upon consideration of the following detailed description of the invention and the accompanying drawings.

DETAILED DESCRIPTION

Figure 1:
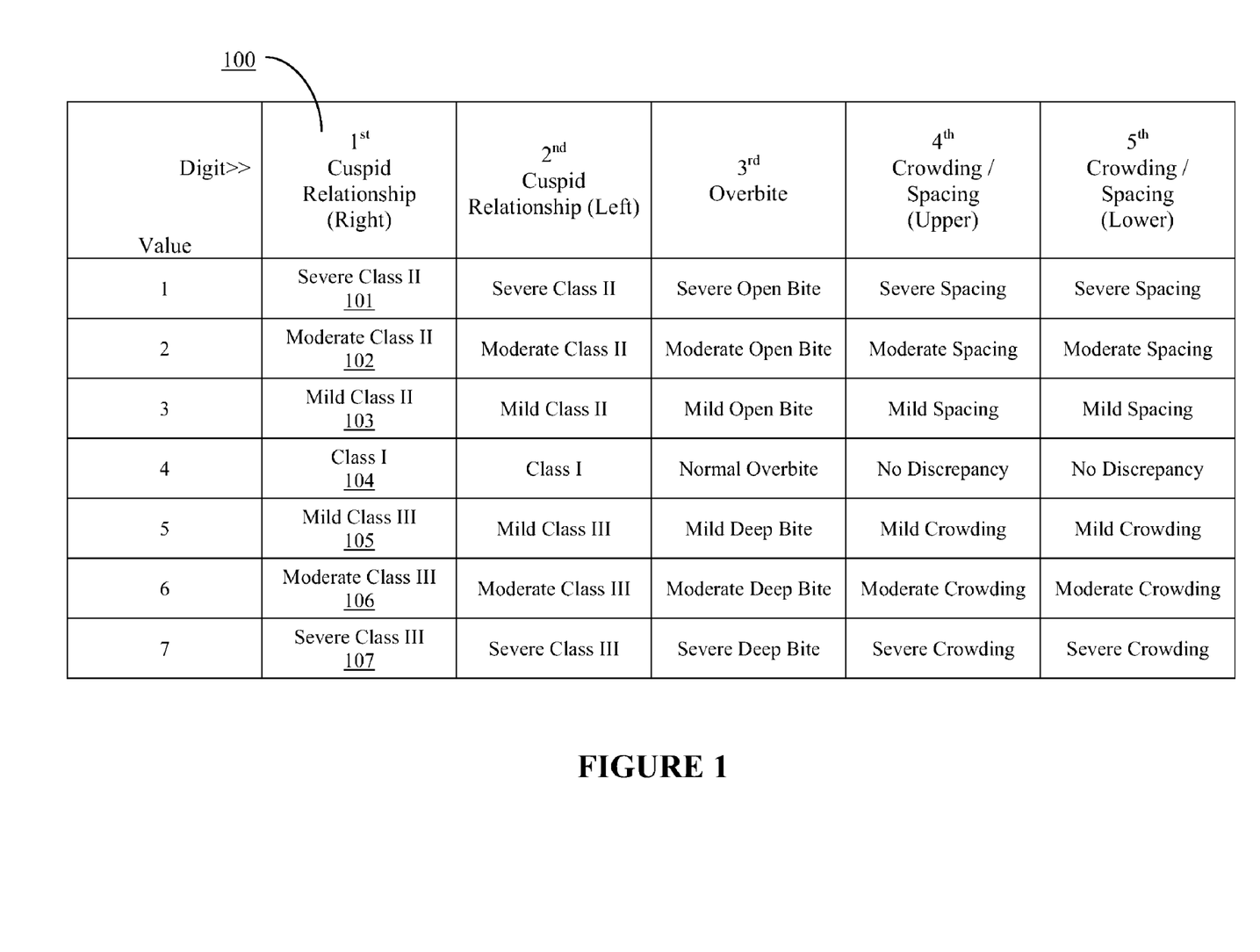
FIG. 1 illustrates a patient's orthodontic condition in accordance with one embodiment of the present disclosure.

FIG. 1 illustrates a patient orthodontic classification system in accordance with one embodiment of the present disclosure. Referring to FIG. 1, in one embodiment, the patient may be classified according to five basic orthodontic parameters—right and left cuspid relationship, anterior vertical overbite, and upper and lower arch length discrepancy. As shown in the Figure, for each of the five orthodontic parameters, one condition may be selected which describes the prospective patient according to five clinical parameters. For example one of the five orthodontic parameters 100 represents the right cuspid relationship and the seven possible conditions 101-107 which the patient can have.

In order for a patient to make an informed decision for choosing a dental professional for orthodontic treatment, it may be advantageous to first determine the expertise, historical success, and/or willingness of the dental professional in treating the patient's actual condition. It may also be helpful to characterize the patient's expectations for treatment with respect to the treatment goal and with respect to the treatment method to be used. Accordingly, in one aspect, the patient's initial condition may be defined or determined. This initial condition may include an assessment that classifies the patient in one or more dental conditions. The assessment may be taken through a consultation, but may also be determined or generated using a self-assessment technique or tool.

In one aspect, the initial patient orthodontic assessment may include a manual visual aid or a computerized visual guide interface system. Additionally, in the computerized visual guide interface system, there are provided one or more databases which have stored therein an index of patients and patient conditions and associated treatments. In this manner, the users may easily obtain a preliminary assessment of a particular patient's orthodontic condition and the associated treatment information based upon the patient's classification.

Additional description related to determination of treatment parameters is provided in U.S. patent application Ser. No. 11/580,536 entitled "Method and System for Providing Dynamic Orthodontic Assessment and Treatment Profiles" filed on Oct. 13, 2006, the disclosure of which is incorporated herein by reference for all purposes.

Figure 2:
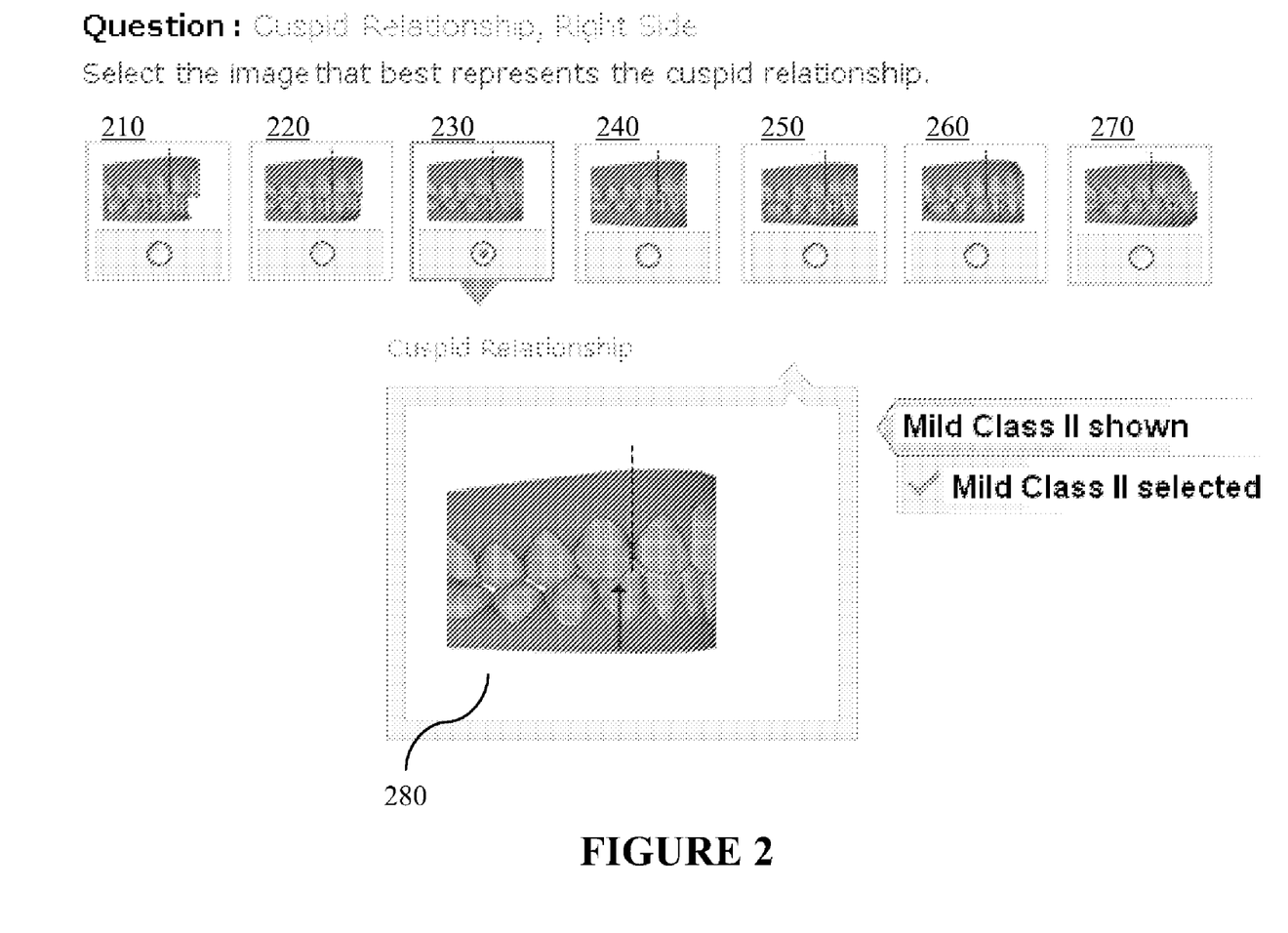
FIG. 2 is an example user interface display for assessing the patient's orthodontic condition in accordance with one embodiment of the present disclosure.

FIG. 2 is an example user interface display for assessing the patient's orthodontic condition in accordance with one embodiment of the present disclosure. Referring to the Figure, the right cuspid relation and seven conditions 200-270 for the patient's right cuspid relationship are shown. Each of the images 200-270 is a visual representation of the seven conditions of the patient's right cuspid relationship. The user selects the image that best represents the patient's actual condition in order to assign a value to the patient's condition for that parameter, for example, as illustrated by the image 280. In one aspect, the user interface displayed may be in the form of a web page, or a worksheet, where the user selects the different parameters that best represents the patient's orthodontic condition, in order to create a patient classification based on the selections. The user interface may be administered by a dental professional, a doctor or staff, or may be a self-assessment by the patient.

Figure 3:
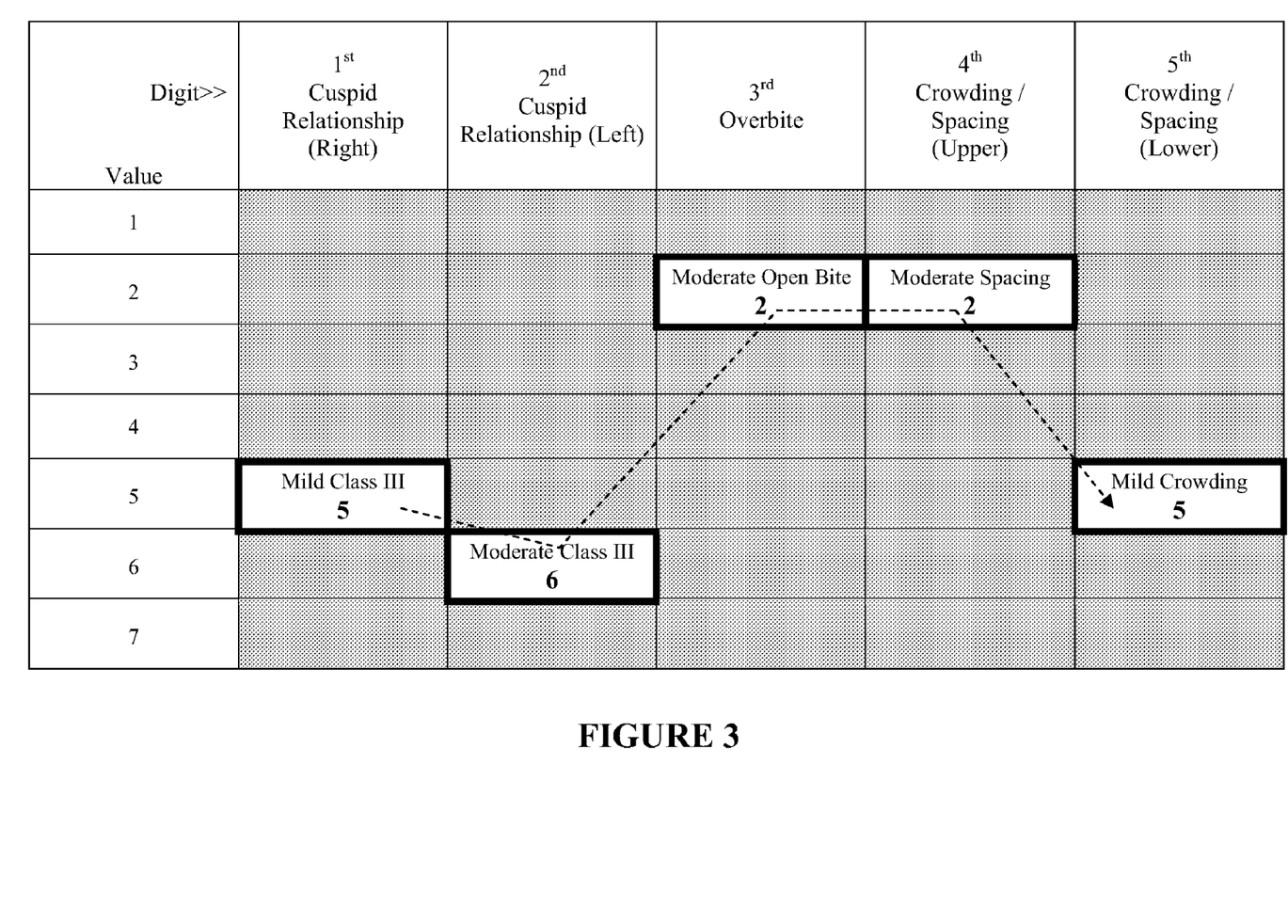
FIG. 3 is an example illustrating generating a five-digit patient classification based on the classification system and user interface in one embodiment.

FIG. 3 is an example illustrating generating a five-digit patient classification based on the classification system and user interface in one embodiment. Referring to FIG. 3, in one aspect, each orthodontic condition is assigned a numerical value ranging from one to seven, and the position of each digit represents the orthodontic parameter itself. That is, in accordance with the classification system discussed above in conjunction with FIG. 1, in one example, the patient belongs to dental classification "56225" (as shown in FIG. 3) which clinically translates to: "mild class III right cuspid relationship, moderate class III left cuspid relationship, moderate vertical overbite, moderate upper spacing arch length discrepancy, mild crowding lower arch length discrepancy."

Figure 4:
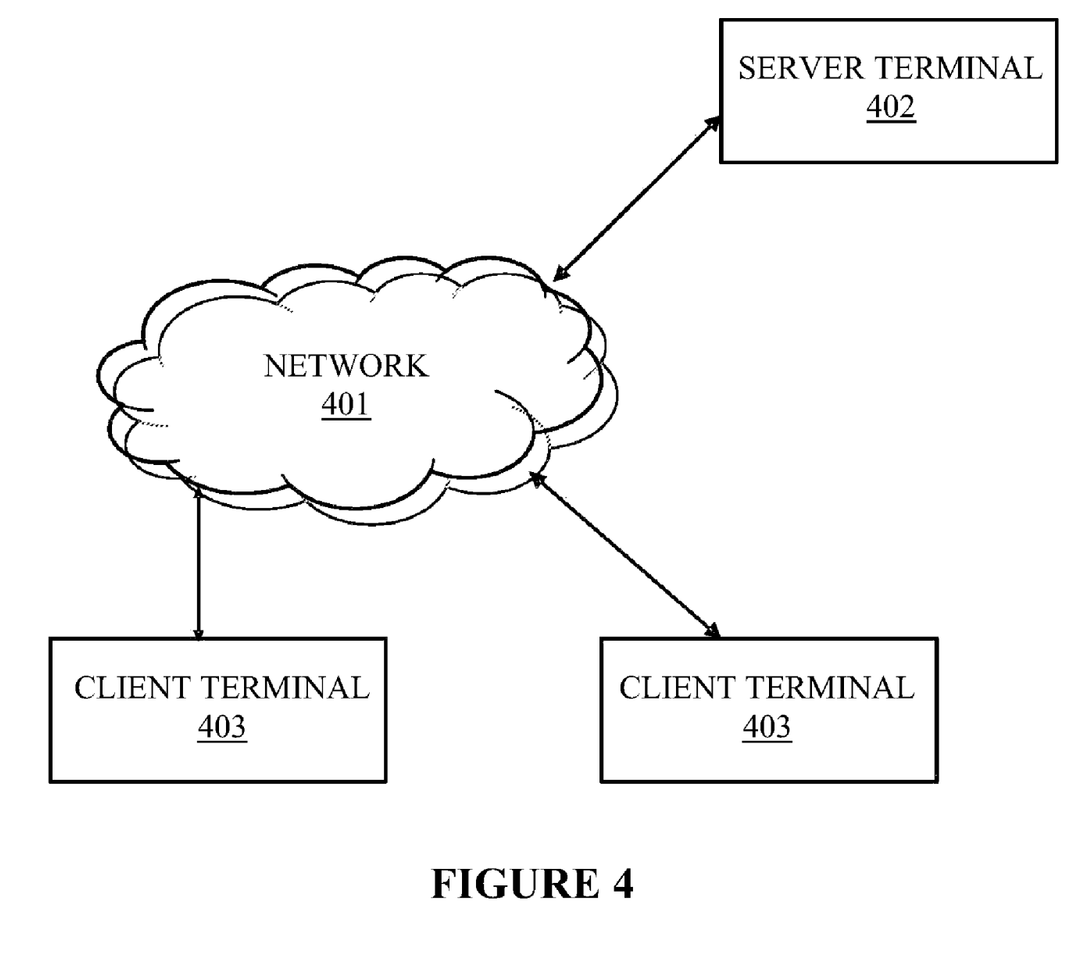
FIG. 4 is a block diagram illustrating an orthodontic self-assessment system in accordance with one embodiment of the present disclosure; illustrates example treatment difficulty categories for orthodontic treatment plans in accordance with one embodiment of the present disclosure.

FIG. 4 is a block diagram illustrating an orthodontic self-assessment system in accordance with one embodiment of the present disclosure. Referring to FIG. 4, the self-assessment system in one embodiment includes a data network 401 and a server terminal 402 operatively coupled to the data network 401. Moreover, one or more client terminals 403 may be provided and operatively coupled to the data network 401. In one embodiment, the one or more client terminals 403 may include a personal computer, a communication enabled booth or kiosk terminal found in public areas such as shopping malls, parks, libraries, and other locations. In one embodiment, the server terminal 402 may be configured to communicate with the one or more client terminals 403 over the data network 401 to receive information related to orthodontic conditions, and provide preliminary assessment related to the treatment options for the orthodontic conditions.

In one embodiment, the client terminal 403 may include a display unit such as a computer display which may be used to visually interact with the user at the client terminal 403 to prompt for the patient specific information related to the patient's orthodontic conditions. Using a web browser or other user interface mechanism on the display unit in conjunction with an input device such as a computer mouse, a keyboard or a touchpad input device, for example, the patient may input the required information, and based upon which, the server terminal 402 may be configured to provide a preliminary assessment as to whether the orthodontic conditions may be treated with aligners such as, for example, polymeric shell aligners, or other methods, and if so, whether there are doctors or clinicians in the local area (or a selected or designated area) that have the necessary experience, success, and/or willingness to perform the desired treatment.

In one embodiment, the patient may be provided with one or more qualified doctors or clinicians that are qualified to treat the patient's orthodontic conditions. Alternatively, the user or the patient may be provided with an option to be contacted by one or more doctors or clinicians (for example, randomly predetermined or selected by the user based on information associated with the one or more doctors). In this case, the user may be prompted to consent to the dissemination of the information that the user has provided at the client terminal 403, and upon consent by the user, the user specific information received from the client terminal 403 may be transmitted to one or more doctors or clinicians that are qualified to treat the user's orthodontic conditions.

Figure 5:
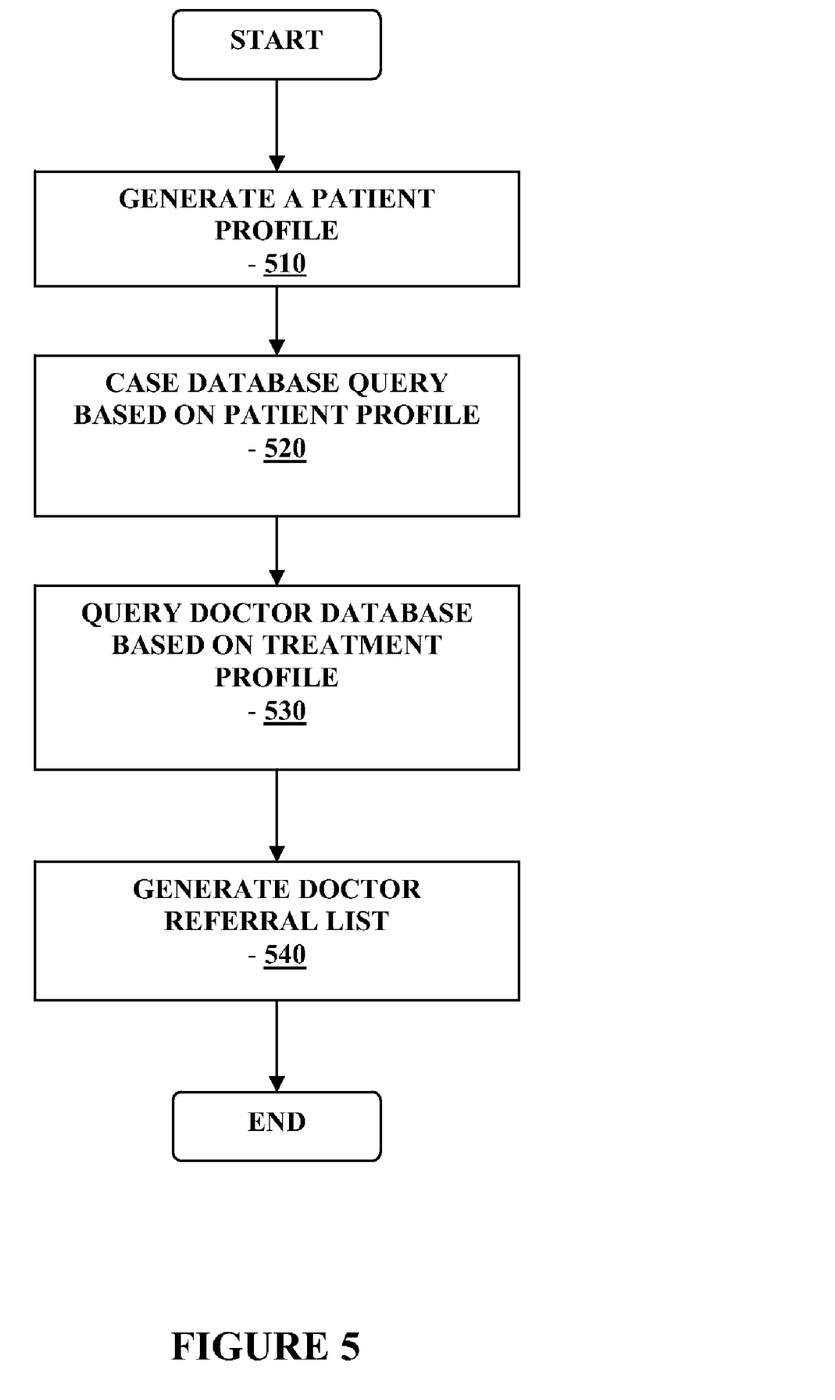
FIG. 5 is a flowchart illustrating an optimized patient referral routine in accordance with one embodiment of the present disclosure.

FIG. 5 is a flowchart illustrating an optimized patient referral routine in accordance with one embodiment of the present disclosure. Referring to FIG. 5, in particular embodiments, a patient profile is generated at step 510 for a prospective orthodontic patient. In one aspect, the patient profile may be automatically or manually generated based on one or more of, for example, the prospective patient's initial orthodontic conditions, the treatment goal, or one or more other treatment parameters including, for example, the desired time period for treatment, the type of treatment plan associated with the desired treatment, cost associated with the treatment, the type of appliance or technique for the treatment, or the prospective patient's desired or preference of treating doctor, for example.

In one aspect, the patient profile may be generated using, for example, a visual interface as described above, which allows the patient or the doctor to examine the prospective patient's initial orthodontic condition by visual examination of the prospective patient's dentition, and comparing the patient's dentition with one or more graphical images illustrating orthodontic conditions that may be substantially similar to the prospective patient's initial orthodontic condition.

Indeed, referring to FIG. 5, at step 520, based on the initial orthodontic condition and/or other treatment parameters associated with the patient profile, a case database query is performed, which may include, for example, retrieving or determining prior treated cases which share same or similar orthodontic conditions and/or treatment parameters. Also using the determined patient profile, at step 520, the database may include data regarding the expected or associated outcomes related to the patient profile selected, including length of treatment, treatment prognosis, common types of treatment plans, and possible complications.

Referring still to FIG. 5, at step 530, based on the initial orthodontic condition and/or other treatment parameters associated with the patient profile, a doctor database is queried. For example, in one embodiment, the doctor database may include the types of cases that the doctor is trained to treat, the types of cases that the doctor is willing to treat, historical information of treatment profiles and/or parameters related to the doctor's treatment history including, for example, the treated patients' initial condition, the goal or target condition, the actual outcome of the treated patients, treatment success rates, and/or parameters related to the to treatments performed including, for example, the duration of treatment, the treatment methodology, any ancillary treatment, types of appliances used in the treatment, and the like.

In one aspect, the doctor profiles stored in the doctor database may be represented in a numerical format, organized by descriptive categorical information, or represented in a combination of descriptive and numerical data associated with each doctor profile. Accordingly, the doctor database in one embodiment includes profiles of doctors and associated treatment parameters including, for example, the range and number of cases that the doctor is willing or trained to perform, the types of treatment goals the doctors have treated, and the statistical history of the doctors' treatment success rates. The doctor database may be used to compare an individual doctor's performance on one or more case performance metrics such as treatment time and level of success achieved relative to the general pool of similar cases found in the case database of step 520.

In one aspect, the doctor database query may include assessments or determinations of the doctors' entire or partial practice pool, where statistical analysis may be performed on the practice pool to determine the scope of the treatment the doctors have performed, the average treatment time per treating case, the number and types of complications that arose with each treatment, the quality of the treatment outcome, and/or whether treatment intervention with traditional fixed orthodontic treatment was necessary.

In this manner, in one aspect, when a prospective patient is identified by a referring doctor, for example, the patient treatment assessment is performed to match the patient profile against a global patient database that includes profiles of patients that have received treatments to determine a similar profile to that of the prospective patient. Based on the determined similar profile of the prior treated case, in one embodiment, the referring doctor may determine a suitable treating doctor who is suitable for recommendation or referral for the treatment of the prospective patient's orthodontic condition.

If the prospective patient has performed a self-evaluation, the patient may be able to find doctors in his or her proximity who have treated similar patients before, and their levels of treatment success, in view of the case database query based on the patient profile (step 520). The patient may also be able to filter doctors based on certain types of data such as minimal levels of success, maximum historical treatment time, or minimal number of similar types of cases treated in the past.

In one embodiment, referring back to FIG. 5, the recommended doctor or list of referral doctors generated at step 540, for example, based on the doctor database query may result from one or more search or query parameters that include treating doctors who are located within a predetermined proximity to the location of the prospective patient, doctors who have treated a certain number of similar cases, as well as other parameters such as the length of the treatment, success rate of the prior treatments, accepted forms of payment (cash, check, credit card, wire transfer and so on), as well as the types of insurance accepted by the doctors. Within the scope of the present disclosure, the query or search parameters to determine the potential list of doctors for the treatment of the prospective patient may be more or less stringent, based on the number of query restrictions or limitations, for each prospective patient, and the associated patient's treatment profile. Some parameters, for example, may be designed at "must have" and others as "nice to have."

In this manner, in one aspect, when one or more doctors for the treatment of the prospective patient's condition is determined, a referral slip may be generated, and optionally, the prospective patient or the prospective patient's referring doctor may forward or transmit the referral slip to the selected one or more doctors determined or identified as described above.

Figure 6:
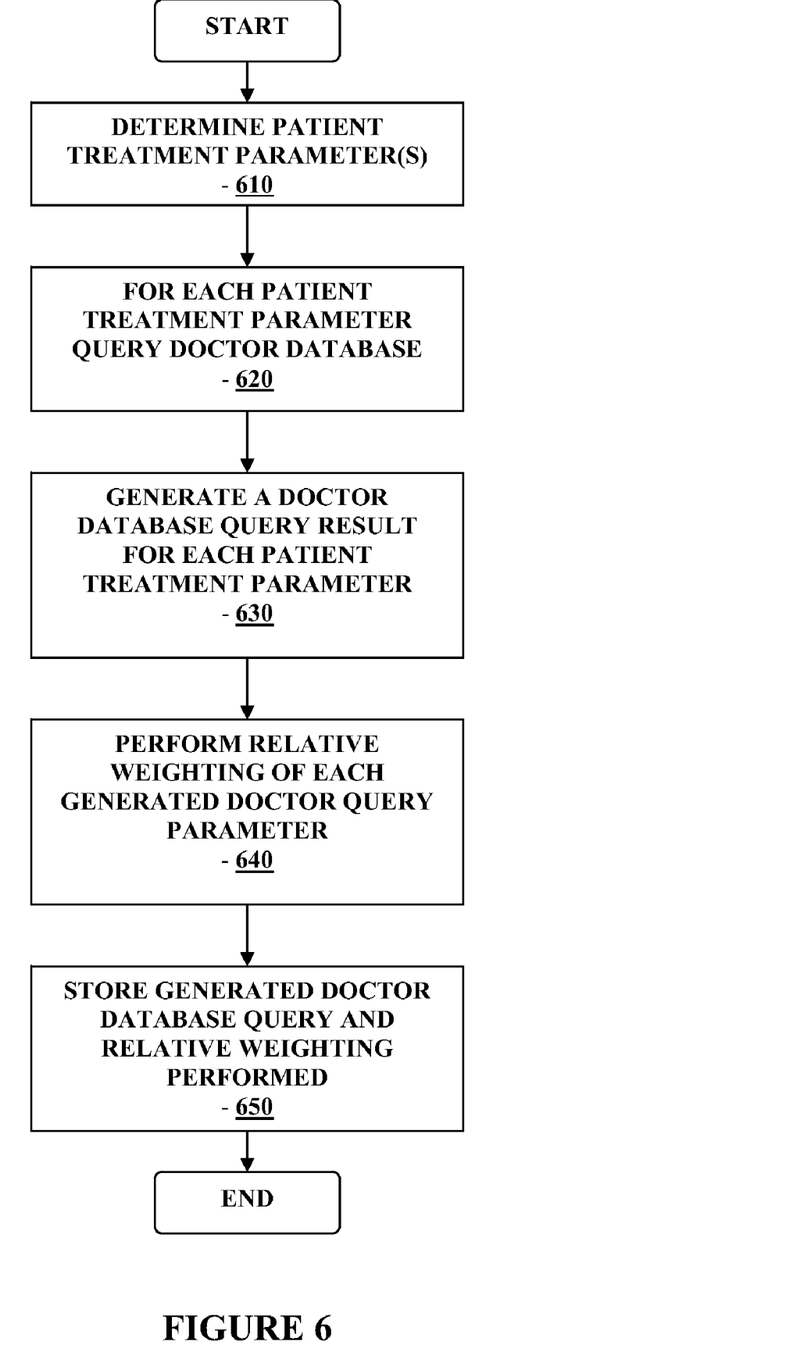
FIG. 6 is a flowchart illustrating the doctor database query routine of the routine described in FIG. 5 in accordance with one embodiment of the present disclosure.

FIG. 6 is a flowchart illustrating the doctor database query routine of the routine described in FIG. 5 in accordance with one embodiment of the present disclosure. Referring to FIG. 6, in one embodiment, one or more patient treatment parameters may be determined at step 610, based, for example, on the treatment profile of the prospective patient. Thereafter, for each treatment parameter, the doctor database may be queried at step 620. Alternatively, one or more searches may be performed to find similar treatment parameter on previously treated patients to determine the corresponding treating doctor who has treated patients with the similar treatment parameter.

Referring back to FIG. 6, at step 630, a doctor database query result is generated for each patient treatment parameter, and thereafter, a relative weighting of each of the generated doctor query parameter is performed 640. For example, if the prospective patient has identified the treatment duration as one of the more important criteria in the treatment of the orthodontic condition, the relative weighting associated with the treatment duration of the doctor's prior treatments would be given a relatively greater weight over one or more other parameters (for example, such as, the cost associated with the treatment, the types of insurance accepted, or any other parameters which the prospective patient has indicated to be of lesser importance than the treatment duration).

Thereafter, the generated doctor database query and the outcome of the relative weighting is optionally stored in a storage unit 650 such as a memory device or transmitted over a data network to a remote location such as a central server or data depository that includes, for example, one or more doctor related or patient related data. Optionally, the data communication over the data network may include data encryption prior to data transmission, and corresponding decryption upon receipt of information over the data network. The encryption/decryption may include, for example, secure socket layer (SSL) encryption/decryption, or any other suitable data security function that protects the information related to the doctor and/or patient.

Figure 7:
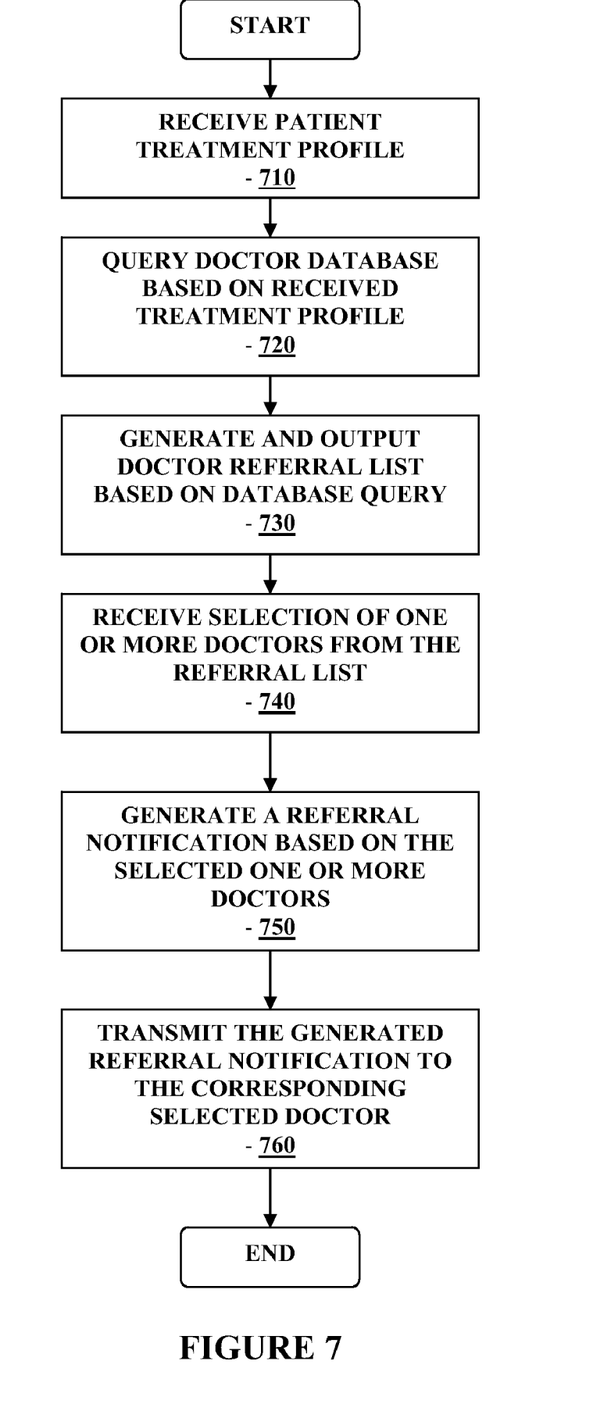
FIG. 7 is a flowchart illustrating optimized patient referral routine with referral notification in accordance with one embodiment of the present disclosure.

FIG. 7 is a flowchart illustrating optimized patient referral routine with referral notification in accordance with one embodiment of the present disclosure. Referring to FIG. 7, in one embodiment, the patient treatment profile is received at step 710, for example, from the patient or the referral doctor. Thereafter, the doctor database is queried based on the treatment profile at step 720, and the resulting doctor referral list based on the database query is generated and output at step 730, for example, on a display screen on the client/user terminal.

Thereafter, when one or more of the doctors listed in the referral list is selected by the prospective patient or the referral doctor, such indication or selection is received at step 740, and based on the selection or indication, a referral notification or referral slip is generated at step 750. Furthermore, as shown in FIG. 7, the generated referral notification in one embodiment may be transmitted to each of the selected one or more doctors in the referral list. In one embodiment, the prospective patient provides authorization to the referral patient to forward or transmit the referral notification or referral slip to the each of the selected one or more doctors. Alternatively, the referral notification or slip may be provided to the prospective patient (for example, as a written or printed notification), in which case, the prospective patient may provide such referral notification or slip to the selected one or more doctors during the prospective patient's visit to the one or more doctors' office.

In a further aspect, the authorization for forwarding the referral notification may be provided as part of the patient profile which is incorporated into the prospective patient's treatment profile. In this case, when the prospective patient selects the one or more doctors determined based on the database query, the referral notification or referral slip may be automatically transmitted or forwarded (for example, over a data network) to the selected one or more doctors 760.

Figure 8:
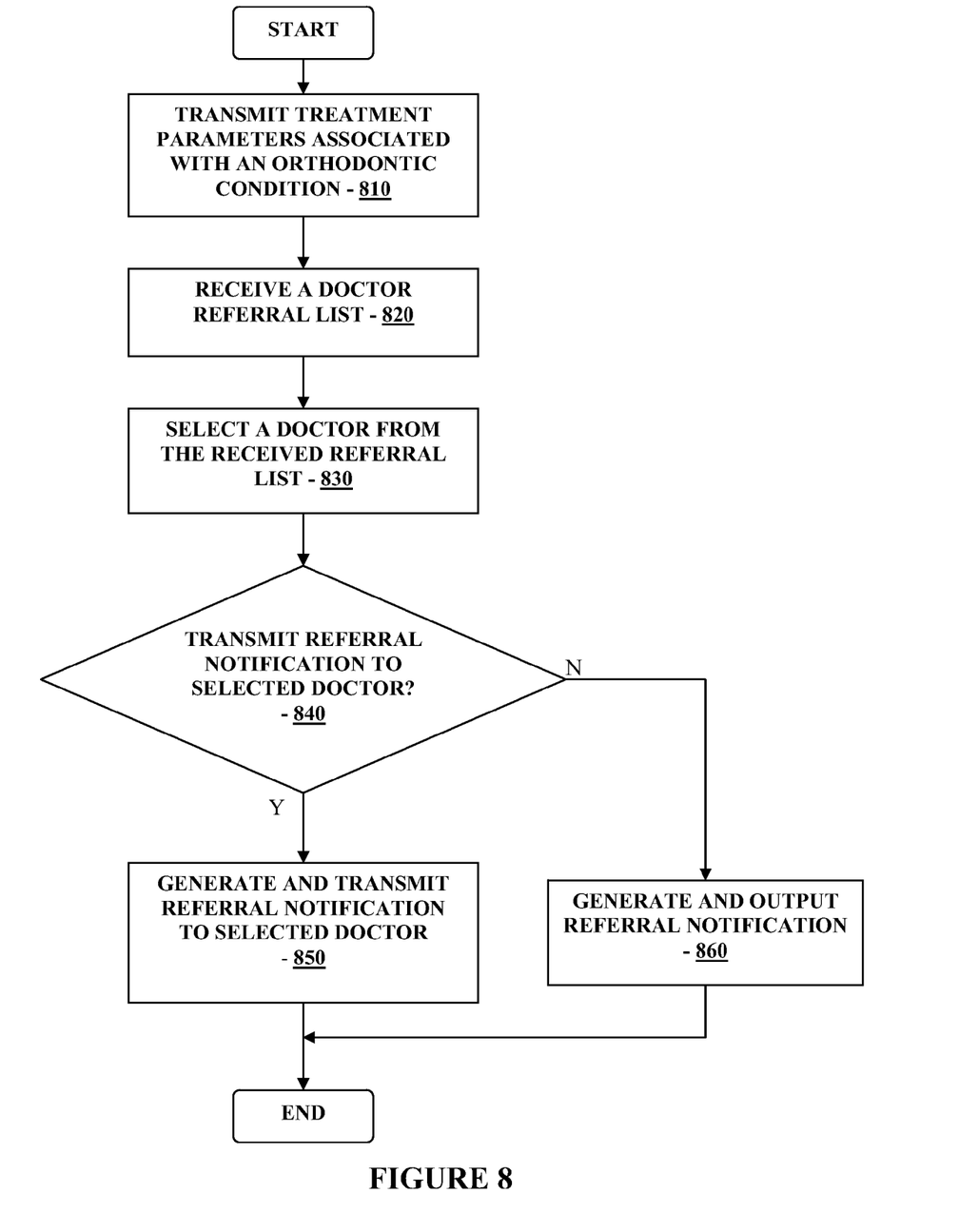
FIG. 8 is a flowchart illustrating the optimized patient referral routine with referral notification function in accordance with another embodiment of the present disclosure.

FIG. 8 is a flowchart illustrating the optimized patient referral routine with referral notification function in accordance with another embodiment of the present disclosure. Referring to FIG. 8, in one embodiment, the treatment parameters associated with a prospective patient's orthodontic condition is transmitted or input using, for example, a user interface of, for example, a client terminal by the prospective patient and/or the referring doctor at step 810. Thereafter, a doctor referral list is received at step 820, for example, as a list of potential doctors that meet the criteria or parameters associated with the treatment of the prospective patient's orthodontic condition.

In one aspect, the list of potential doctors may be displayed on the display unit of the client terminal and for example, may include, doctor profile information associated with each identified doctor in the referral list. For example, each doctor identified in the displayed referral list may include the doctor's office location, number of similar cases (as that of the prospective patient's orthodontic condition) treated, success rate of the treated similar cases, educational background of the doctor, the accepted types of insurance and/or payment options, for example, which may be listed or displayed for each identified doctor and optionally ranked or organized in the order of importance or significance to the prospective patient (for example, based on the prospective patient's treatment parameters).

Upon selection of one or more of the doctors from the received referral list at step 830, the prospective patient in one embodiment is prompted to select whether or not to transmit the referral notification or referral slip to the selected one or more doctors identified in the referral list at step 840. If the prospective patient selects the transmit option to forward the referral notification to the selected one or more doctors at step 840, the referral notification is generated and transmitted to the selected one or more doctors at step 850, for example, over a data network to the selected one or more doctors' office computer terminal, for example, connected to the data network.

Referring to FIG. 8, if at step 840, the prospective patient decides to not transmit the referral notification to the selected one or more doctors from the referral list, then at step 860, the referral notification is generated and provided to the prospective patient (to take to the respective one or more doctors' office during the subsequent initial visit therewith).

In the manner described, in one aspect of the present disclosure, prospective patients with particular orthodontic conditions may be matched to a list of potentially well trained and suitable doctors that have a history of treating similar conditions, and also, who meet or at least satisfy some or all of the treatment parameters defined by the prospective patient such as, for example, the treatment duration, treatment cost, doctor's educational background, the doctor's experience level, and the like.

In a further aspect, the approach for matching prospective patients to a network or list of potential doctors may include providing a patient referral network using, for example, a web-based patient self-assessment tool which allows the prospective patient to perform preliminary self assessment of the orthodontic condition using, for example, a graphical interface, or by visiting a self-assessment kiosk. While the self assessment approach may not be as accurate or comprehensive as compared to an assessment performed by a referral doctor, in one aspect, the database queries based on the assessed treatment profile of the prospective patient may provide sufficient information to provide a referral to a group of doctors that are willing to treat the prospective patient's orthodontic condition and who have treated such conditions in the past.

Accordingly, in one aspect, a more appropriate or accurate matching between potential or prospective orthodontic patients and the treating doctors may be achieved, and further, increase the probability of finding or locating one or more doctors that are well suited to treat the prospective patient's orthodontic condition. With the doctors who are open to have their practice profiled and indexed in, for example, a database for subsequent queries, the doctors may be provided with incentives to expand treatment options provided, increase the range or types of treatments qualified to treat, and thereby potentially increasing the likelihood of receiving referrals based on the querying and searching approaches as described above.

A computer implemented method in one embodiment includes generating a doctor profile based on one or more parameters associated with the doctor treatment information, generating an orthodontic patient profile based at least in part on a weighting of a plurality of orthodontic related treatment parameters, and providing one or more doctor referrals based on the generated doctor profile and the generated orthodontic patient profile.

The doctor treatment information in one aspect may include historical orthodontic treatment information of prior treated patients, and further, where the historical orthodontic treatment information of prior treated patients may be related at least in part to the one or more parameters associated with the doctor treatment information.

In one embodiment, the weighting of the plurality of orthodontic related treatment parameters may be performed dynamically based, at least in part on one or more of an initial orthodontic related condition of the patient, a final orthodontic related condition of the patient, or an ideal orthodontic related condition of the patient.

Furthermore, in one aspect, generating the doctor profile may include retrieving the one or more parameters associated with the doctor treatment information. Also, the one or more parameters may include one or more of the doctor treatment skill level, the doctor treatment comfort level, the number of patients treated by the doctor for each level of treatment difficulty, the treatment success rate of the doctor, the location of the doctor's office, the cost associated with the doctor's treatment, the doctor's treatment experience, the doctor's educational background, the doctor's proficiency in spoken or written language, the doctor's professional status, or the ADA compliance status of the doctor's office.

Additionally, generating the orthodontic patient profile may include querying one or more databases based on at least the one or more parameters associated with the patient profile to determine one or more corresponding doctor profiles, wherein one embodiment, querying the one or more databases may include establishing match between the patient profile and the corresponding one or more doctor profiles.

A computer implemented method in accordance with another embodiment includes generating an orthodontic patient profile, performing a treatment assessment based on the patient profile to determine a treatment profile, querying a database based on the treatment profile, and generating a list of referral doctors associated with the treatment profile.

In one embodiment, generating the orthodontic patient profile may include receiving one or more parameters associated with an initial orthodontic condition of the patient, an ideal orthodontic condition of the patient, or a treatment preference of the patient.

In still another aspect, performing the treatment assessment may include generating a treatment plan associated with the treatment profile.

Furthermore, in yet another aspect, querying the database may include retrieving from the database one or more doctor information associated with the treatment profile, where each of the one or more doctor information may include treatment history information associated with the treatment profile.

The method in a further embodiment may include generating a doctor profile, the list of referral doctors including the generated doctor profile.

Also, the method may also include outputting the list of referral doctors.

Additionally, the method may include generating a referral notification including at least one of the doctors in the generated list of referral doctors.

A computer implemented method in accordance with still another embodiment includes determining one or more treatment parameters associated with an orthodontic condition of a patient, querying a database for each of the one or more treatment parameters, generating a query result for each treatment parameter, and weighting each of the query result based on a predetermined weighting parameter.

In one embodiment, querying the database may include searching a doctor database for doctor treatment history associated with the one or more treatment parameters.

An apparatus in accordance with yet still another embodiment includes a data storage unit, and a data processing unit operatively coupled to the data storage unit, the data processing unit configured to generate a doctor profile based on one or more parameters associated with the doctor treatment information, generate an orthodontic patient profile based at least in part on a weighting of a plurality of orthodontic related treatment parameters, and to provide one or more doctor referrals based on the generated doctor profile and the generated orthodontic patient profile.

In one embodiment, the data processing unit may be configured to perform the weighting of the plurality of orthodontic related treatment parameters based, at least in part on one or more of an initial orthodontic related condition of the patient, a final orthodontic related condition of the patient, or an ideal orthodontic related condition of the patient.

The data processing unit in a further aspect may be configured to retrieve the one or more parameters associated with the doctor treatment information from the data storage unit.

Additionally, the data processing unit may be configured to query one or more databases stored in the data storage unit based on at least the one or more parameters associated with the patient profile to determine one or more corresponding doctor profiles.

The data processing unit in still another aspect may be configured to establish a match or correlation between the patient profile and the corresponding one or more doctor profiles.

The apparatus may also include an output unit operatively coupled to the data processing unit, where the output unit is configured to output information associated with the one or more doctor referrals based on the generated doctor profile and the generated orthodontic patient profile.

In one embodiment, the output unit may include a display unit such as a computer monitor, an LCD screen, or the like for displaying or visually outputting information to the prospective patient and/or the referring doctor.

The output information may include one or more of text information or graphical information.

The apparatus may also include a data communication unit operatively coupled to the data processing unit, the data communication unit configured to transmit data associated with the one or more doctor referrals to a remote location.

The remote location in one aspect may include one or more of a central server terminal or a client terminal.

An apparatus in accordance with yet still a further embodiment includes a data storage unit, and a data processing unit operatively coupled to the data storage unit, the data processing unit configured to generate an orthodontic patient profile, perform a treatment assessment based on the patient profile to determine a treatment profile, query a database in the data storage unit based on the treatment profile, and generate a list of referral doctors associated with the treatment profile.

In a further aspect, the data processing unit may be configured to receiver one or more parameters associated with an initial orthodontic condition of the patient, a treatment goal of the patient, or a treatment preference of the patient.

In yet another embodiment, the data processing unit may be configured to generate a treatment plan associated with the treatment profile.

The data processing unit may be configured to retrieve from the database one or more doctor information associated with the treatment profile, where each of the one or more doctor information may include treatment history information associated with the treatment profile.

The data processing unit may be configured to generate a doctor profile, the list of referral doctors including the generated doctor profile.

Also, the data processing unit may be configured to output the list of referral doctors.

Additionally, the data processing unit may be configured to generate a referral notification including at least one of the doctors in the generated list of referral doctors.

An apparatus in accordance with another aspect includes a data storage unit, and a data processing unit operatively coupled to the data storage unit, the data processing unit configured to determine one or more treatment parameters associated with an orthodontic condition of a patient, query a database for each of the one or more treatment parameters, generate a query result for each treatment parameter, and weigh each of the query result based on a predetermined weighting parameter.

The data processing unit may be configured to search a doctor database for doctor treatment history associated with the one or more treatment parameters, where the doctor database may be stored in the data storage unit.

The apparatus may include a data communication unit operatively coupled to the data processing unit configured to query the database at a remote location using the data communication unit, where the data communication unit may be operatively coupled to a data network.

In this manner, in accordance with aspects of the present disclosure, there is provided a method for receiving one or more dentition conditions of a patient, generating a patient classification and searching for doctors based on the doctor's frequency of treating said classification based on their actual treated patient's history.

Another embodiment of the present disclosure may include receiving one or more dentition conditions of a patient, generating a patient classification and searching for doctors based on the doctor's previous success in treating said classification in their actual treated patient's history. Further, yet another embodiment of the present disclosure may include receiving one or more dentition conditions of a patient, generating a patient classification and searching for doctors based on the doctor's stated willingness to treat patients of said classification types.

Moreover, in still another aspect of the present disclosure may include receiving one or more dentition conditions of a patient, defining one or more treatment goals based on the one or more dentition conditions, searching for doctors based on the combination of initial and goal condition, and the doctor's experience, past success, and/or willingness to treat such combinations.

In yet a further embodiment may include receiving one or more dentition conditions of a patient, defining one or more treatment methods (e.g. extraction, non-extraction) based on the one or more dentition conditions, searching for doctors based on the combination of initial condition and method, and the doctor's experience, past success, and/or willingness to treat such combinations.

In still a further aspect of the present disclosure may include receiving one or more dentition conditions of a patient, defining one or more goals, and one or more treatment methods (e.g. extraction, non-extraction) based on the one or more dentition conditions, and searching for doctors based on the combination of initial condition, treatment goal, and treatment method, the doctor's experience, past success, and/or willingness to treat such combinations.

Various other modifications and alterations in the structure and method of operation of this invention will be apparent to those skilled in the art without departing from the scope and spirit of the invention. Although the invention has been described in connection with specific preferred embodiments, it should be understood that the invention as claimed should not be unduly limited to such specific embodiments. It is intended that the following claims define the scope of the present disclosure and that structures and methods within the scope of these claims and their equivalents be covered thereby.

What is claimed is:

1. A computer implemented method, comprising:
    generating a doctor profile of a doctor based on one or more parameters associated with treatment information of the doctor, wherein the treatment information comprises historical orthodontic treatment information of prior treated patients, wherein the generating of the doctor profile is performed by a computer;
    generating a patient dental profile of a patient based at least in part on a weighting of a portion of a plurality of orthodontic-related treatment parameters, the generating of the patient dental profile being performed by the computer and comprising:
        assigning a value to each orthodontic condition of a first set of orthodontic conditions to achieve an assigned set of values comprising a patient classification, the first set of orthodontic conditions being a selected set of current orthodontic conditions of the patient, wherein the position of each value within the assigned set of values represents an orthodontic-related treatment parameter of the plurality of orthodontic-related treatment parameters;
        receiving an identification of a set of orthodontic-related treatment parameters of the plurality of orthodontic-related treatment parameters that is important to the patient in the treatment of the first set of orthodontic conditions;
        weighting the set of orthodontic-related treatment parameters relative to the plurality of orthodontic-related treatment parameters; and
    providing one or more doctor referrals based on the generated doctor profile and the generated patient dental profile, wherein the providing the one or more doctor referrals is performed by the computer and comprises:
        determining which of the prior treated patients has a second set of orthodontic conditions similar to the first set of orthodontic conditions.

2. The method of claim 1 wherein the historical orthodontic treatment information of prior treated patients is related at least in part to the one or more parameters associated with the treatment information of the doctor.

3. The method of claim 1 wherein weighting of the plurality of orthodontic-related treatment parameters is performed dynamically based, at least in part on one or more of an initial orthodontic-related condition of the patient, a final orthodontic-related condition of the patient, or a desired orthodontic-related condition of the patient.

4. The method of claim 1 wherein generating the doctor profile includes retrieving the one or more parameters associated with the treatment information of the doctor.

5. The method of claim 1 wherein the one or more parameters includes one or more of a treatment skill level of the doctor, a treatment comfort level provided by the doctor, a number of patients treated by the doctor for each level of treatment difficulty, a treatment success rate of the doctor, a location of an office of the doctor, a cost associated with the treatment by the doctor, a method of payment accepted by the doctor, a treatment experience provided by the doctor, an educational background of the doctor, a proficiency in a spoken or written language by the doctor, a professional status of the doctor, or an American Dental Association compliance status of the office of the doctor.

6. The method of claim 1 wherein the generating the patient dental profile includes querying one or more databases based on at least the one or more parameters associated with the patient dental profile to determine one or more corresponding doctor profiles.

7. The method of claim 6 wherein the querying the one or more databases includes establishing a match between the patient dental profile and the corresponding one or more doctor profiles.

8. The method of claim 6 wherein the one or more databases includes data or information associated with one or more of a treatment skill level of the doctor, a treatment comfort level provided by the doctor, a number of patients treated by the doctor for each level of treatment difficulty, a treatment success rate of the doctor, a location of an office of the doctor, a cost associated with a treatment by the doctor, a method(s) of payment accepted by the doctor, a treatment experience associated with the doctor, an educational background of the doctor, a proficiency in spoken or written language of the doctor, a professional status of the doctor, or an American Dental Association compliance status of the office of the doctor.

9. A computer implemented method, comprising:
    generating a patient dental profile of a patient based at least in part on a weighting of a portion of a plurality of orthodontic-related treatment parameters, the generating of the patient dental profile is performed by a computer and comprising:
        assigning a value to each orthodontic condition of a first set of orthodontic conditions to achieve an assigned set of values comprising a patient classification, the first set of orthodontic conditions being a selected set of current orthodontic conditions of the patient, wherein the position of each value within the assigned set of values represents an orthodontic-related treatment parameter of the plurality of orthodontic-related treatment parameters;

receiving an identification of a set of orthodontic-related treatment parameters of the plurality of orthodontic-related treatment parameters that is important to the patient in the treatment of the first set of orthodontic conditions; and weighting the set of orthodontic-related treatment parameters relative to the plurality of orthodontic-related treatment parameters;

performing a treatment assessment based on the patient profile to determine a treatment profile;

querying a database based on the treatment profile, the querying the database includes retrieving from the database one or more doctor information associated with the treatment profile, each of the one or more doctor information includes treatment history information associated with the treatment profile, wherein the querying is performed by the computer;

generating a list of referral doctors associated with the treatment profile, wherein the generating the list of referral doctors is performed by the computer and comprises:

determining which of the prior treated patients has a second set of orthodontic conditions similar to the first set of orthodontic conditions; and generating a doctor profile, the list of referral doctors including the generated doctor profile.

10. The method of claim 9 wherein generating the patient dental profile includes receiving one or more parameters associated with an initial orthodontic condition of the patient, a treatment goal of the patient, or a treatment preference of the patient.

11. The method of claim 10 wherein performing the treatment assessment includes generating a treatment plan associated with the treatment profile.

12. The method of claim 9 further including outputting the list of referral doctors.

13. The method of claim 9 further including generating a referral notification including at least one of the doctors in the generated list of referral doctors.

14. A computer implemented method, comprising:

determining one or more orthodontic treatment parameters of a patient dental profile of a patient, the one or more orthodontic treatment parameters based at least in part on a weighting of a portion of a plurality of orthodontic treatment parameters, wherein the determining of the one or more orthodontic treatment parameters is performed by a computer and, comprises:

assigning a value to each orthodontic condition of a first set of orthodontic conditions to achieve an assigned set of values comprising a patient classification, the first set of orthodontic conditions being a selected set of current orthodontic conditions of the patient, wherein the position of each value within the assigned set of values represents an orthodontic treatment parameter of the one or more orthodontic treatment parameters; and receiving an identification of a set of orthodontic treatment parameters of the one or more orthodontic treatment parameters that is important to the patient in the treatment of the first set of orthodontic conditions;

querying a database for each of the one or more orthodontic treatment parameters, wherein the querying is performed by the computer;

generating a query result for each of the one or more orthodontic treatment parameters, wherein the generating is performed by the computer, and wherein the generating a query result comprises:

determining which doctor treatment history corresponds to the first set of orthodontic conditions; and weighting each of the query results based on the identification of the set of orthodontic treatment parameters, wherein the weighting is performed by the computer.

15. The method of claim 14 wherein the querying the database includes searching a doctor database for the doctor treatment history associated with the one or more orthodontic treatment parameters.

16. An apparatus, comprising:

a data storage unit; and a data processing unit operatively coupled to the data storage unit, the data processing unit configured for:

generating a doctor profile of a doctor based on one or more parameters associated with treatment information of the doctor, wherein the treatment information comprises historical orthodontic treatment information of prior treated patients;

generating an orthodontic patient profile of a patient based at least in part on a weighting of a portion of a plurality of orthodontic-related treatment parameters, the generating of the orthodontic patient profile comprising:

assigning a value to each orthodontic condition of a first set of orthodontic conditions to achieve an assigned set of values comprising a patient classification, the first set of orthodontic conditions being a selected set of current orthodontic conditions of the patient, wherein the position of each value within the assigned set of values represents an orthodontic-related treatment parameter of the plurality of orthodontic-related treatment parameters;

receiving an identification of a set of orthodontic-related treatment parameters of the plurality of orthodontic-related treatment parameters that is important to the patient in the treatment of the first set of orthodontic conditions;

weighting the set of orthodontic-related treatment parameters relative to the plurality of orthodontic-related treatment parameters; and providing one or more doctor referrals based on the generated doctor profile and the generated orthodontic patient profile, wherein the providing the one or more doctor referrals comprises:

determining which of the prior treated patients has a second set of orthodontic conditions similar to the first set of orthodontic conditions.

17. The apparatus of claim 16 wherein the data processing unit is configured to perform the weighting of the plurality of orthodontic related treatment parameters based, at least in part on one or more of an initial orthodontic related condition of the patient, a final orthodontic related condition of the patient, or a desired orthodontic-related condition of the patient.

18. The apparatus of claim 16 wherein the data processing unit is further configured to retrieve the one or more parameters associated with the treatment information of the doctor from the data storage unit.

19. The apparatus of claim 16 wherein the one or more parameters includes one or more of a treatment skill level of the doctor, a treatment comfort level of the doctor, a number of patients treated by the doctor for each level of treatment difficulty, a treatment success rate of the doctor, location of an office of the doctor, a cost associated with a treatment by the doctor, method of payment accepted by the doctor, a treatment experience provided by the doctor, an educational background of the doctor, a proficiency in spoken or written language by the doctor, a professional status of the doctor, or an American Dental Association compliance status of the office of the doctor.

20. The apparatus of claim 16 wherein the data processing unit is further configured to query one or more databases stored in the data storage unit based on at least the one or more parameters associated with the orthodontic patient profile to determine one or more corresponding doctor profiles.

21. The apparatus of claim 20 wherein the data processing unit is further configured for establishing a match between the orthodontic patient profile and the corresponding one or more doctor profiles.

22. The apparatus of claim 20 wherein the one or more databases includes data or information associated with one or more of a treatment skill level of the doctor, a treatment comfort level of the doctor, a number of patients treated by the doctor for each level of treatment difficulty, a treatment success rate of the doctor, a location of an office of the doctor, a cost associated with a treatment, a method of payment accepted by the doctor, a treatment experience provided by the doctor, an educational background of the doctor, a proficiency in spoken or written language of the doctor, a professional status of the doctor, or an American Dental Association compliance status of the office of the doctor.

23. The apparatus of claim 16 further including an output unit operatively coupled to the data processing unit, wherein the output unit is configured for outputting information associated with the one or more doctor referrals based on the generated doctor profile and the generated orthodontic patient profile.

24. The apparatus of claim 16 further including a data communication unit operatively coupled to the data processing unit, the data communication unit configured for transmitting data associated with the one or more doctor referrals to a remote location.

25. An apparatus, comprising:
a data storage unit; and
a data processing unit operatively coupled to the data storage unit, the data processing unit configured for:
generating a patient dental profile of a patient based at least in part on a weighting of a portion of a plurality of orthodontic-related treatment parameters, the generating of the patient dental profile comprising:
assigning a value to each orthodontic condition of a first set of orthodontic conditions to achieve an assigned set of values comprising a patient classification, the first set of orthodontic conditions being a selected set of current orthodontic conditions of the patient, wherein the position of each value within the assigned set of values represents an orthodontic-related treatment parameter of the plurality of orthodontic-related treatment parameters;
receiving an identification of a set of orthodontic-related treatment parameters of the plurality of orthodontic-related treatment parameters that is important to the patient in the treatment of the first set of orthodontic conditions; and
weighting the set of orthodontic-related treatment parameters relative to the plurality of orthodontic-related treatment parameters;
perform performing a treatment assessment based on the patient profile to determine a treatment profile;
querying a database in the data storage unit based on the treatment profile, the querying the database includes retrieving from the database one or more doctor information associated with the treatment profile, each of the one or more doctor information includes treatment history information associated with the treatment profile;
generate generating a list of referral doctors associated with the treatment profile, wherein the generating the list of referral doctors comprises:
determining which of the prior treated patients has a second set of orthodontic conditions similar to the first set of orthodontic conditions; and
generating a doctor profile, the list of referral doctors including the generated doctor profile.

26. The apparatus of claim 25 wherein the data processing unit is configured for receiving one or more parameters associated with an initial orthodontic condition of the patient, a treatment goal of the patient, or a treatment preference of the patient.

27. The apparatus of claim 26 wherein the data processing unit is further configured for generating a treatment plan associated with the treatment profile.

28. The apparatus of claim 25 wherein the data processing unit is further configured for outputting the list of referral doctors.

29. The apparatus of claim 25 wherein the data processing unit is further configured for generating a referral notification including at least one of the doctors in the generated list of referral doctors.

30. An apparatus, comprising:
a data storage unit; and
a data processing unit operatively coupled to the data storage unit, the data processing unit configured for:
determining one or more orthodontic treatment parameters of a patient dental profile of a patient, the one or more orthodontic treatment parameters based at least in part on a weighting of a portion of a plurality of orthodontic treatment parameters, wherein the determining of the one or more orthodontic treatment parameters comprises:
assigning a value to each orthodontic condition of a first set of orthodontic conditions to achieve an assigned set of values comprising a patient classification, the first set of orthodontic conditions being a selected set of current orthodontic conditions of the patient, wherein the position of each value within the assigned set of values represents an orthodontic treatment parameter of the one or more orthodontic treatment parameters; and
receiving an identification of a set of orthodontic treatment parameters of the one or more orthodontic treatment parameters that is important to the patient in the treatment of the first set of orthodontic conditions;
querying a database for each of the one or more orthodontic treatment parameters;
generating a query result for each of the one or more orthodontic treatment parameters, and wherein the generating a query result comprises:
determining which doctor treatment history corresponds to the first set of orthodontic conditions; and
weighting each of the query results based on the identification of the set of orthodontic treatment parameters.

31. The apparatus of claim 30 wherein the data processing unit is further configured for searching a doctor database for the doctor treatment history associated with the one or more orthodontic treatment parameters.

32. The apparatus of claim 31 further including a data communication unit operatively coupled to the data processing unit configured for querying the database at a remote location using the data communication unit.

* * * * *

UNITED STATES PATENT AND TRADEMARK OFFICE
CERTIFICATE OF CORRECTION

| | | |
|---|---|---|
| PATENT NO. | : 8,024,198 B2 | Page 1 of 1 |
| APPLICATION NO. | : 12/258125 | |
| DATED | : September 20, 2011 | |
| INVENTOR(S) | : Eric Kuo | |

It is certified that error appears in the above-identified patent and that said Letters Patent is hereby corrected as shown below:

In the Claims:

Col. 15, Line 66, Claim 25: Delete "perform"

Col. 16, Line 8, Claim 25: Delete "generate"

Signed and Sealed this
Twenty-second Day of November, 2011

David J. Kappos
*Director of the United States Patent and Trademark Office*